United States Patent [19]
Rubbers et al.

[11] Patent Number: 5,961,277
[45] Date of Patent: Oct. 5, 1999

[54] INSPECTION DEVICE AND METHOD

[75] Inventors: Philippe Rubbers; Nicolaas Stephanus Kruger, both of Johannesburg, South Africa

[73] Assignee: Eskom, South Africa

[21] Appl. No.: 08/885,683

[22] Filed: Jun. 30, 1997

[51] Int. Cl.[6] .................................................. G01N 21/00
[52] U.S. Cl. ...................... 415/118; 415/201; 356/241.1
[58] Field of Search .................... 415/118, 201; 376/248; 73/634, 633, 640, 621; 356/241.1, 241.2

[56] References Cited

U.S. PATENT DOCUMENTS

| | | | |
|---|---|---|---|
| 3,841,764 | 10/1974 | Snell et al. | 356/241.1 |
| 4,255,762 | 3/1981 | Takeyasu et al. | 356/241.1 |
| 4,729,423 | 3/1988 | Martin | 376/248 |
| 5,504,788 | 4/1996 | Brooks et al. | 376/248 |

FOREIGN PATENT DOCUMENTS 58-93968   6/1983   Japan ...................................... 415/118

*Primary Examiner*—F. Daniel Lopez
*Assistant Examiner*—Richard Woo
*Attorney, Agent, or Firm*—Londa and Traub LLP

[57] ABSTRACT

There is provided an inspection device and method for inspecting a pump having a casing defining an internal surface and a plurality of radially spaced diffuser vanes arranged within the casing. The inspection device includes an image providing apparatus for providing a remote picture of surfaces of the vanes and the internal surface of the casing, and a maneuverable carrier apparatus for carrying the image providing apparatus, which is sufficiently manoeuvrable to pass into a space defined between adjacent diffuser vanes and beyond.

23 Claims, 4 Drawing Sheets

INSPECTION DEVICE AND METHOD

FIELD OF THE INVENTION

THIS INVENTION relates to an inspection device and to a method of inspection. More particularly, the invention relates to an inspection device for inspecting a pump having a casing defining an internal surface and a plurality of radially spaced diffuser vanes arranged within the casing, and to a method of inspecting such pumps.

BACKGROUND TO THE INVENTION

A known high volume liquid pump includes a casing having an inlet and an outlet and a plurality of radially spaced diffuser vanes arranged about a central vertically orientated axis within the casing and spaced from the axis. In a typical embodiment of such a pump, the inlet is defined in a bottom wall of the casing and the outlet in a side of the casing. The diffuser vanes are positioned in a region of the pump casing below a top of the casing. An impeller is mounted inward of the vanes, to rotate about the central vertical axis of the casing. A cylindrical guide sleeve, known as a casing adaptor or water guide, is mounted between the inlet and the diffuser vanes, coaxial with the central axis, to provide a conduit between the inlet and the impeller.

Pumps of the type described are used in the coolant systems of pressurised water reactors in nuclear power stations. It will be appreciated that such pumps require regular inspection of the internal surface of the casing and of the surfaces of the diffuser vanes. Further, such pumps may be radioactively contaminated.

It is known to inspect the internal surface of the casing and the diffuser vanes of a pump of the type described, by means of a remotely operated and manoeuvrable inspection device having a video camera mounted thereon, the device being mounted within the casing above the inlet. In order to mount the known device in position, a removable portion of the top of the casing is required to be removed and the impeller and the casing adaptor removed via the top of the casing.

It will be appreciated that removal of the casing adaptor is particularly difficult and time consuming and may lead to exposure to radiation. In particular, casing adaptor locking cups must be removed, followed by casing adaptor bolts. Where the casing adaptor bolts have seized, such bolts must be machined out, using a specialized device. The radioactive casing adaptor must be extracted and stored. In practice, damage to various components, such as a split ring, may occur in the removal of the casing adaptor, necessitating repair to such components. After removal of the casing adaptor, as described, and visual inspection of the internal surface of the casing and diffuser vanes, the casing adaptor must be re-installed. The casing adaptor bolts must be replaced and torqued to specification, and the locking cups replaced.

By means of the present invention the internal surface of the casing and the diffuser vanes are inspected via the diffuser vanes, thereby obviating removal of the casing adaptor. By eliminating the need for removal of the casing adaptor, down time of the reactor is reduced. Also, the need to machine-out seized bolts and retrieve components such as broken locking cups which have fallen into the casing, in obviated. Further, the possibility of incorrect torquing of the bolts or replacement of the locking cups is eliminated.

SUMMARY OF THE INVENTION

According to a first aspect of the invention, there is provided an inspection device for inspecting a pump having a casing defining an internal surface and a plurality of radially spaced diffuser vanes arranged within the casing, the inspection device including an image providing means for providing a remote picture of surfaces of the vanes and the internal surface of the casing; and a manoeuvrable carrier means for carrying the image providing means, which is sufficiently manoeuvrable to pass into a space defined between adjacent diffuser vanes and beyond.

The carrier means may comprise an elongate member which is insertable into the space between the vanes. In particular, the member may be an arm. Where the vanes are curved, the arm may be curved to correspond with curvature of the vanes.

The arm may be retractably extendable and may be remotely operable to retract and extend.

The inspection device may include a support means, the arm being attached thereto. The arm may be displaceably mounted on the support means and may be remotely operable to be displaced relative to the support means.

The support means may comprise a base member mountable on the casing, and an elongate guide means extending transversely from the base member, the arm being mounted on the guide means. The arm may be mounted cantilever fashion and may extend laterally from the guide means.

The guide means may be displaceably mounted on the base member. In particular, the guide means may be displaceable to orbit about a transverse axis through a point defined upon the base member, and radially displaceable relative to the said point. The guide means may define a longitudinal axis and may also be rotatable about the said longitudinal axis. The arm may be displaceable along the guide means.

The image providing means may be mounted on a free end of the arm. The image providing means may be displaceably mounted on the arm. In particular, the arm may define a longitudinal axis at its free end and the image providing means may be displaceable to revolve about the said axis and to tilt relative to the said axis. In a preferred embodiment of the invention, the image providing means may be a video camera.

According to second aspect of the invention, there is provided a method of in situ inspection of a pump having a casing defining an internal surface and a plurality of radially spaced diffuser vanes arranged within the casing, the method including the steps of passing an image providing means into a space defined between adjacent diffuser vanes and beyond;

scanning at least a portion of the internal surface of the casing with the image providing means; and generating a picture of the scanned surface.

The method may include also scanning portions of the vane surfaces.

Where the pump being inspected includes an impeller, the method may include the step of removing the impeller.

Where the image providing means is carried by a manipulatable manoeuvrable carrier means which is sufficiently manoeuvrable to pass into and beyond the space between the vanes, the method may include the step of manipulating the carrier means into and beyond the said space.

The carrier means may be remotely manipulated.

Where the carrier means is supported by a support means, the method may included the step of mounting the support means on the casing.

The invention is now described, by way of example, with reference to the accompanying diagrammatic drawings.

DETAILED DESCRIPTION OF THE DRAWINGS

Figure 1:
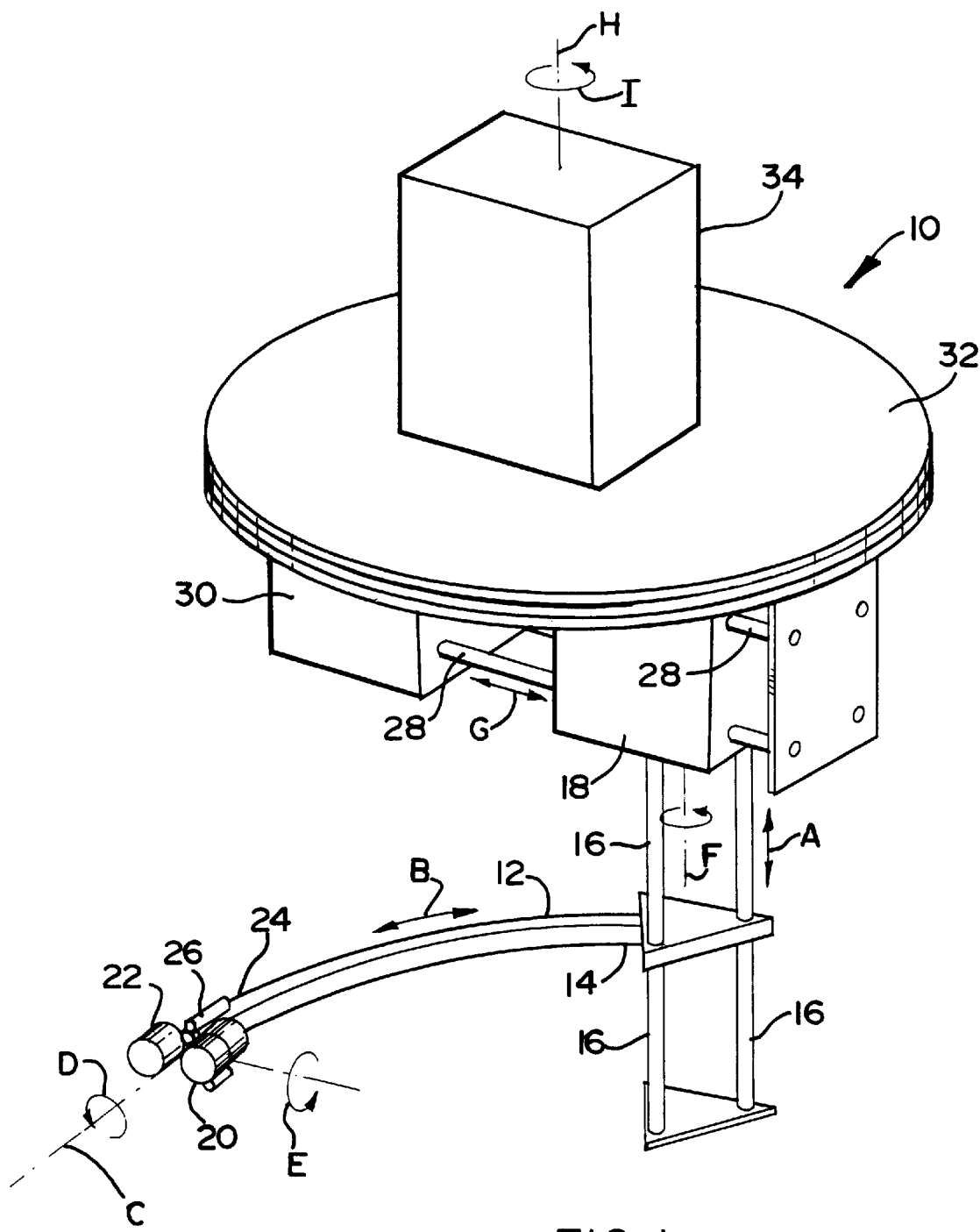
FIG. 1 shows a three-dimensional view of an inspection device for inspecting a pump having a casing defining an internal surface and a plurality of diffuser vanes arranged within the casing, in accordance with the invention.

In the drawings reference numeral 10 generally refers to an inspection device for inspecting a pump having a casing defining an internal surface and a plurality of diffuser vanes arranged within the casing, in accordance with the invention.

The inspection device 10, as illustrated in FIG. 1, has an arm 12 which is curved in an operatively horizontal plane, to pass between adjacent diffuser vanes of the pump. A first end 14 of the arm 12 is displaceably mounted on three parallel guide shafts 16, the arm 12 being displaceable axially along the shafts 16 as indicated by arrow A. The arm 12 is displaced by means of a first servo motor (not shown) which is contained in a housing 18, the motor being remotely operable. A video camera 20 and light source 22 are mounted on a free end 24 of the arm 12. The arm 12 is retractably extendable as indicated by arrow B. The video camera 20 and light source 22 are displaceable in concert relative to the arm 12 by means of a second electric servo motor (not shown) to revolve about a longitudinal axis C defined by the arm at its free end 24, as indicated by the arrow D. The video camera 20 and light source 22 are further displaceable in concert relative to the arm 12 by means of a third electric servo motor 26 to tilt relative to the longitudinal axis C, as indicated by the arrow E.

The guide shafts 16 are mounted on a travelling table (not shown) housed within the housing 18 and are revolvable about a longitudinal axis F defined by the guide shafts 16 and co-parallel with the guide shafts 16, by means of fourth electric servo motor (not shown) mounted within the housing 18. The travelling table is mounted on a set of four parallel second guide shafts 28 to be axially displaceable along the shafts 28 as indicated by the arrow G, by means of a fifth electric servo motor (not shown) mounted in a second housing 30. The second guide shafts 30 and the travelling table are mounted on a generally planar base member 32 and rotatable about a central axis H, perpendicular to the plane of the base member 32, as indicated by arrow I, by means of a sixth electric servo motor 34. Each of the abovementioned servo motors are independently remotely actuated.

Figure 3:
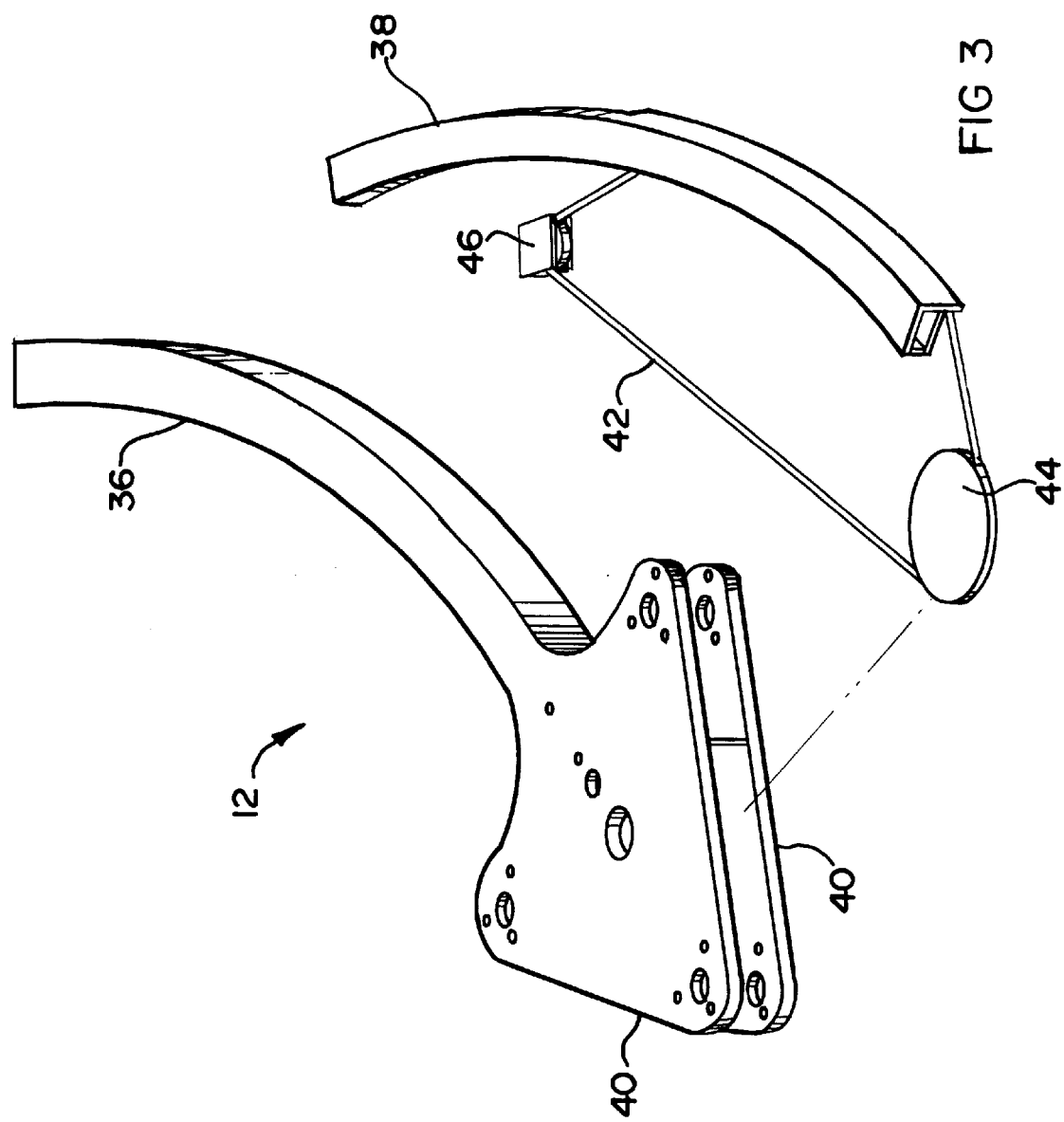
FIG. 3 shows a three-dimensional view of an inspection arm for the device.

Turning now to FIG. 3, the arm 12 comprises a sheath 36 and a sliding member 38, which is slidably received within the sheath 36, the arm 12 being operable to extend and retract telescope fashion by displacing the sliding member 38 longitudinally relative to the sheath 36. The arm 12 is attached to, and projects from a pair of triangular formations 40, which are mounted on the first guide shafts 16, in use. The sliding member 38 is operated by means of a chain 42, ends of which are attached thereto, the chain passing around a drive cog 44 and a tensioning cog 46, both of which are rotatably mounted on and within the sheath 36.

Figure 2:
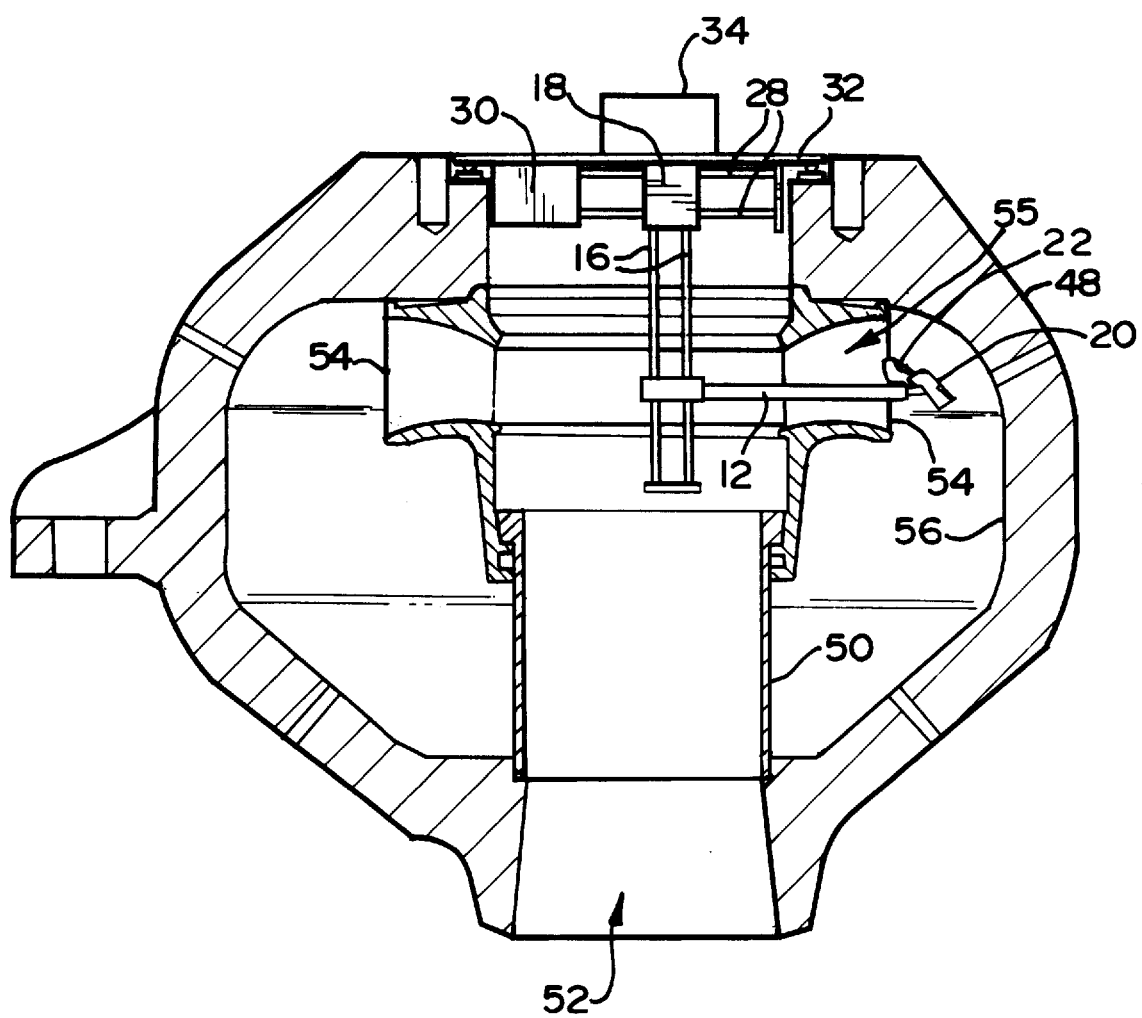
FIG. 2 shows a sectional side view of the inspection device installed on the pump casing.

In use, as illustrated in FIG. 2, equipment normally mounted atop the casing 48 is removed, allowing the base member 32 to be mounted on top of the casing 48. A casing adaptor 50 mounted between the pump inlet 52 and a plurality of radially spaced diffuser vanes 54 is left in place. An impeller (not shown) is removed. The arm 12 is manipulated by remote control of the servo motors to extend into the space 55 defined between adjacent diffuser vanes 54 and beyond. The camera 20 and light source 22 are manoeuvred to tilt and rotate, thereby scanning the internal surface 56 of the casing 48 and portions of the surfaces 58 of the diffuser vanes 54. Pictures of the scanned surfaces 56 and 58 are generated and displayed on a video monitor (not shown).

Figure 4:
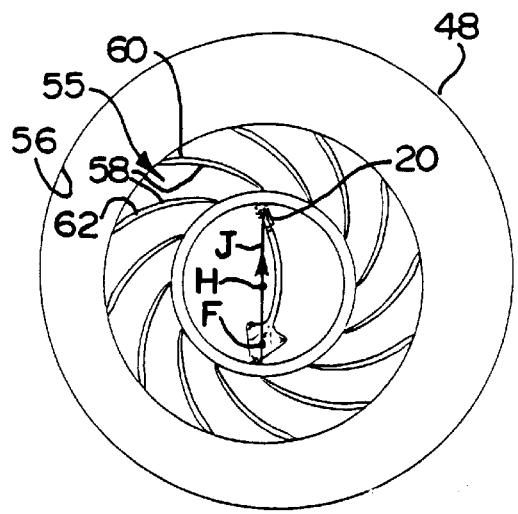
FIG. 4 shows a sectional plan view of the inspection arm and pump casing, with the inspection arm in position before manipulation of the arm into a space defined between adjacent diffuser vanes.
Figure 5:
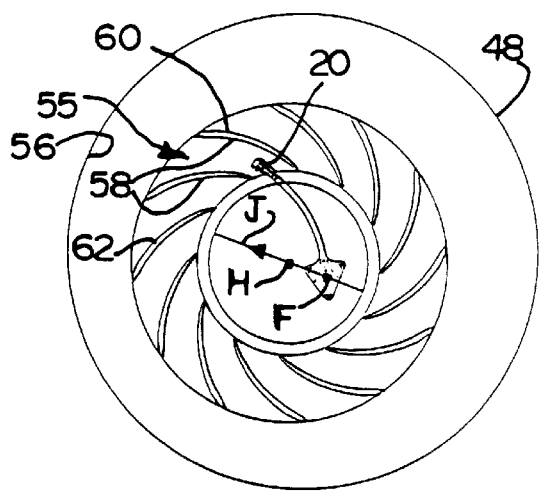
FIG. 5 shows a sectional plan view of the inspection arm and pump casing, with the inspection arm partly manipulated between adjacent diffuser vanes.
Figure 6:
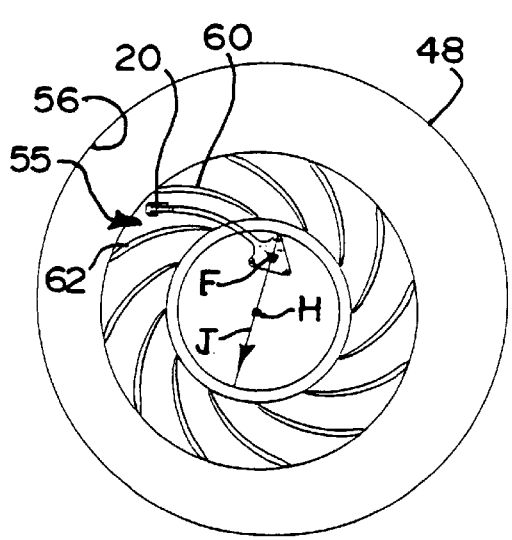
FIG. 6 shows a sectional plan view of the inspection arm and pump casing, with the inspection arm fully manipulated between adjacent diffuser vanes.
Figure 7:
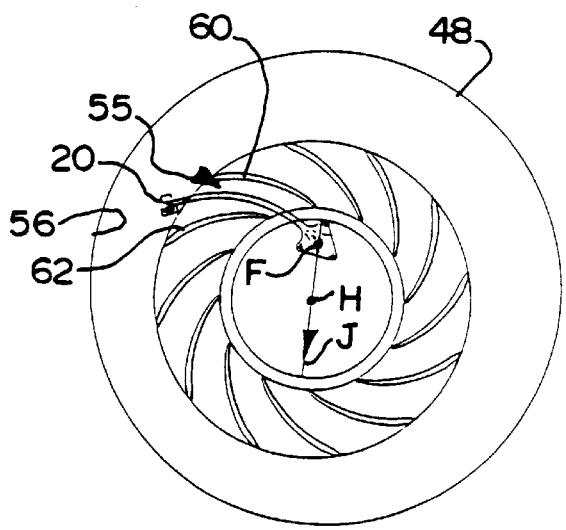
FIG. 7 shows a sectional plan view of the inspection arm and pump casing, with the inspection arm fully manipulated between adjacent diffuser vanes and the arm fully extended.

Referring to FIGS. 4 to 7, the inspection device 10 is mounted on the casing 48, as described above. FIG. 4 shows the arm 12 of the inspection device 10 in an initial position to inspect the surfaces 58 of adjacent vanes 60 and 62, as well as the internal surface 56 of the casing 48. A reference axis J is drawn through the longitudinal axis F of the guide shafts 16 and the central axis H of the base member 32. In FIG. 5, the arm 12 has been displaced towards the central axis H, as well as being revolved about the central axis H, thereby introducing the video camera 20 into the space 55 between the adjacent vanes 60 and 62. In FIG. 6, further rotation of the arm 12 about the central axis H and displacement of the arm 12 away from the central axis H has resulted in the further intrusion of the camera 20 into the space 55. Finally, as shown in FIG. 7, the arm 12 is extended, permitting the camera 20 to project beyond the vanes 60 and 62 and enable the internal surface 56 to be scanned. It will be appreciated that, at the stages illustrated, and at intermediate stages, portions of the surfaces 58 of the vanes 60 and 62 are scanned by the camera 20. Once the camera 20 is in the position shown in FIG. 7, as described above, it is tilted and rotated to scan the adjacent internal surface of the casing 48. Once the adjacent internal surface has been scanned, the arm 12 is retracted and withdrawn, and inserted between the next set of vanes 54. The process is repeated until the entire internal surface 56 of the casing 48 has been scanned and inspected.

We claim:

1. An inspection device for inspecting a pump having a casing defining an internal surface and a plurality of radially spaced curved diffuser vanes arranged within the casing, the inspection device including an image providing means for providing a remote picture of surfaces of the vanes and the internal surface of the casing; and a maneuverable carrier means for carrying the image providing means, the carrier means comprising an arm which is smoothly curved to correspond with the curvature of the vanes and which is sufficiently maneuverable to pass into a space defined between adjacent diffuser vanes and beyond.

2. The inspection device as claimed in claim 1, in which the arm is retractably extendable.

3. The inspection device as claimed in claim 2, in which the arm is remotely operable to retract and extend.

4. The inspection device as claimed in claim 3, which includes a support means, the arm being attached thereto.

5. The inspection device as claimed in claim 4, in which the arm is displaceably mounted on the support means.

6. The inspection device as claimed in claim 5, in which the arm is remotely operable to be displaced relative to the support means.

7. The inspection device as claimed in claim 4, in which the support means comprises a base member mountable on the casing, and an elongate guide means extending transversely from the base member, the arm being mounted on the guide means.

8. The inspection device as claimed in claim 7, in which the guide means is displaceably mounted on the base member.

9. The inspection device as claimed in claim 8, in which the guide means is displaceable to orbit about a transverse axis through a point defined upon the base member, and radially displaceable relative to the said point.

10. The inspection device as claimed in claim 9, in which the guide means defines a longitudinal axis and is rotatable about the said longitudinal axis.

11. The inspection device as claimed in claim 10, in which the arm is displaceable along the guide means.

12. The inspection device as claimed in claim 10, in which the arm is mounted cantilever fashion and extends laterally from the guide means.

13. The inspection device as claimed in claim 2, in which the arm comprises two telescopically inter-connected curved elements.

14. The inspection device as claimed in claim 1, in which the image providing means is mounted on a free end of the arm.

15. The inspection device as claimed in claim 14, in which the image providing means is displaceably mounted on the arm.

16. The inspection device as claimed in claim 15, in which the arm defines a longitudinal axis at its free end and the image providing means is displaceable to revolve about the said axis and to tilt relative to the said axis.

17. The inspection device as claimed in claim 1, in which the image providing means is a video camera.

18. A method of in situ inspection of a pump having a casing defining an internal surface and a plurality of radially spaced smoothly curved diffuser vanes arranged within the casing, the method including the steps of manipulating a maneuverable carrier comprising an arm which is smoothly curved to correspond with the curvature of the vanes and having an image providing means mounted thereon into a space defined between adjacent diffuser vanes and beyond;

scanning at least a portion of the internal surface of the casing with the image providing means; and generating a picture of the scanned surface.

19. The method claimed in claim 18, which includes also scanning portions of the vane surfaces.

20. The method claimed in claim 19, in which the pump has an impeller and which includes the step of removing the impeller.

21. The method claimed in claim 18, in which the carrier means is remotely manipulated.

22. The method claimed in claim 18, in which the carrier means is supported by a support means, which includes mounting the support means on the casing.

23. An inspection device for inspecting a pump having a casing defining an internal surface and a plurality of radially spaced curved diffuser vanes arranged within the casing, the inspection device including an image providing means for providing a remote picture of surfaces of the vanes and the internal surface of the casing; and a maneuverable carrier means for carrying the image providing means, the carrier means comprising a non-articulated curved arm maneuverable to pass into a space defined between adjacent diffuser vanes and beyond.

* * * * *